(12) United States Patent
Hara et al.

(10) Patent No.: US 8,105,840 B2
(45) Date of Patent: Jan. 31, 2012

(54) URINE PRETREATMENT AGENT FOR URINARY PROTEIN QUANTITATION, URINE PRETREATMENT METHOD, AND URINARY PROTEIN QUANTITATION METHOD

(75) Inventors: Masanori Hara, Niigata (JP); Akihiko Saito, Niigata (JP); Shinya Ogasawara, Niigata (JP); Yoshiaki Hirayama, Niigata (JP); Hiroyuki Kurosawa, Niigata (JP)

(73) Assignees: Niigata University (JP); Masanori Hara (JP); Denka Seiken Co., Ltd. (JP)

( * ) Notice: Subject to any disclaimer, the term of this patent is extended or adjusted under 35 U.S.C. 154(b) by 61 days.

(21) Appl. No.: 12/680,479

(22) PCT Filed: Sep. 26, 2008

(86) PCT No.: PCT/JP2008/067422
§ 371 (c)(1),
(2), (4) Date: Mar. 26, 2010

(87) PCT Pub. No.: WO2009/041577
PCT Pub. Date: Apr. 2, 2009

(65) Prior Publication Data
US 2010/0233738 A1 Sep. 16, 2010

(30) Foreign Application Priority Data

Sep. 27, 2007 (JP) ................................ 2007-251707

(51) Int. Cl.
*G01N 33/68* (2006.01)
*G01N 33/48* (2006.01)

(52) U.S. Cl. .................. 436/86; 436/8; 436/17; 436/18; 436/63; 252/408.1

(58) Field of Classification Search ................ 436/8, 15, 436/18, 63, 86, 17; 252/408.1; 435/7.92
See application file for complete search history.

(56) References Cited

U.S. PATENT DOCUMENTS 5,385,847 A   1/1995   Yip et al.

| | | | |
|---|---|---|---|
| 2003/0045003 A1* | 3/2003 | Smith | 436/518 |
| 2004/0058395 A1* | 3/2004 | Hara | 435/7.2 |
| 2007/0177146 A1* | 8/2007 | Fujimoto | 356/338 |

FOREIGN PATENT DOCUMENTS

| | | |
|---|---|---|
| EP | 1813931 | 1/2007 |
| JP | 06-011507 | 1/1994 |
| JP | 08-170960 | 7/1996 |
| JP | 10-507269 | 7/1998 |
| JP | 10-282095 | 10/1998 |
| JP | 11-153602 | 6/1999 |
| JP | 2000-352565 | 12/2000 |
| JP | 2007-205732 | 8/2007 |
| WO | 97/08549 A1 | 3/1997 |
| WO | 02/37099 A1 | 5/2002 |
| WO | 2007/119563 A1 | 10/2007 |

OTHER PUBLICATIONS

Kobayashi et al., Conditions for Solubilization of Tamm-Horsfall Protein/Uromodulin in Human Urine and Establishment of a Sensitive and Accurate Enzyme-Linked Immunosorbent Assay (ELISA) Method, Biochem. & Phys., Apr. 1, 2001, pp. 113-120, vol. 388, No. 1.

Norden et al., Urinary Megalin Deficiency Implicates Abnormal Tubular Endocytic Function in Fanconi Syndrome, J. Am. Soc. Nephrol., 2002, vol. 13, pp. 125-133.

Kanno, Katsue, "Urinary Sediment Podocalyxin in Children with Mesangial Proliferative Glomerulonephritis", Niigata Medical Journal, 2002, vol. 116, No. 5, pp. 219-227.

* cited by examiner

*Primary Examiner* — Maureen Wallenhorst
(74) *Attorney, Agent, or Firm* — Akerman Senterfitt

(57) ABSTRACT

Described are a urine pretreatment agent, a urine pretreatment method, and a urinary protein quantitation method which reduce or cancel the influences of urine pH variations, cancel the influences of precipitates of urinary inorganic salts, and solubilize membrane proteins. The urine pretreatment agent for urinary protein quantitation, includes a buffer, a chelating agent, and a surfactant; the urine pretreatment method includes a step of mixing 10 to 1000 parts by mass of the urine pretreatment agent of the present invention with 100 parts by mass of urine; and the urinary protein quantitation method includes steps of: mixing 10 to 1000 parts by mass of the urine pretreatment agent with 100 parts by mass of urine; and then measuring the protein concentration.

9 Claims, 3 Drawing Sheets

Buffer concentration and pH variation

Podocalyxin measurement system:
Measurement accuracy evaluation with or without urine pretreatment Podocalyxin measurement system : pH dependence Megalin measurement system :
Measurement accuracy evaluation with or without urine pretreatment Megalin measurement system : pH dependence Effect of surfactant addition

URINE PRETREATMENT AGENT FOR URINARY PROTEIN QUANTITATION, URINE PRETREATMENT METHOD, AND URINARY PROTEIN QUANTITATION METHOD

TECHNICAL FIELD

The present invention relates to a urine pretreatment agent for urinary protein quantitation, a urine pretreatment method, and a urinary protein quantitation method.

BACKGROUND ART

Measurement of urinary proteins is not only useful for the diagnosis of diseases and pathological conditions of the kidney and urinary system but also of the circulatory system and other organs in the entire body. It is known, however, that the measurement of urinary proteins is affected by the variations in the pH, inorganic salts and other low molecular weight components in the urine. The pH, inorganic salts, and other low molecular weight components vary due to the pathological conditions. In the prior art neat urine is extensively diluted with a buffer solution for the measurement of urinary proteins, in order to reduce the effect of the urine composition. Some of the urinary proteins drawing recent attention are present in urine in low concentration and are hardly detectable if they are extensively diluted as in the prior art.

Podocalyxin, a functional molecule expressed in the glomerulus epithelial cells, plays an important role in keeping the function and morphology of the glomerulus. Patent Document 1 discloses a method for measuring human podocalyxin in a sample, comprising: reacting the sample with first anti-human podocalyxin antibody linked to a solid phase; reacting with second anti-human podocalyxin monoclonal antibody of which corresponding epitope is different from that of the first anti-human podocalyxin antibody; and measuring the second anti-human podocalyxin monoclonal antibody bound to the solid phase. The technique has problems that it cannot quantitate a trace amount of urinary podocalyxin, because the urine sample in almost neat concentration cannot be employed in the quantitation system; that accurate quantitative analysis of the urine sample cannot be carried out due to the deposition or accumulation of the inorganic salt precipitates derived from the urine sample, because the urine is not pretreated with the a chelating agent; and that the total podocalyxin content in the urine cannot be quantitated, because the solubilization with a surfactant is not carried out.

Patent Document 1: Japanese Unexamined Patent Application Publication No. 6-011507

Patent Document 2 discloses a stabilizing preservative solution for urine αGST comprising a non-enzymatic protein in an amount enough for urine αGST stabilization, a chelating agent, and a buffer, thereby the reservative solution has the pH of 7.0 to 7.5, and is effective for preventing the loss of immunological activity of αGST. The technique has problems that accurate quantitative analysis cannot be carried out, because the urine pH is not completely compensated or homogenized; that accurate quantitative analysis cannot be carried out, because the precipitates of inorganic salts in the urine sample are not completely dissolved; and that membrane proteins present in the urine containing membrane components cannot be quantitated.

Patent Document 2: Published Japanese translation of PCT international application No. 10-507269

Patent Document 3 discloses a method for stabilizing urinary myoglobin and a preservative used in the method, the method comprising: adding to a urine sample a compound(s) selected from the group consisting of alkali metal azides, metal chelating agents, albumin, and saccharose. The technique has problems that accurate quantitative analysis cannot be carried out, because the urine pH is not completely compensated or homogenized; that accurate quantitative analysis cannot be achieved because the precipitates of inorganic salts in the urine sample are not completely dissolved; and that membrane proteins present in the urine containing membrane components cannot be quantitated.

Patent Document 3: Japanese Unexamined Patent Application Publication No. 10-282095

Patent Document 4 describes a method for stabilizing analytes in a urine sample, and a preservative for a urine sample using the method, the stabilizing method comprising: adding a urine sample a reducing oxygen acid salt and/or an isothiazolone compound, containing a buffer or an alkaline chemical, adjusting the pH value of the urine sample in the range of 6 to 9, and further containing a chelating agent. The technique has problems that accurate quantitative analysis cannot be carried out, because the urine pH is not completely compensated or homogenized; that accurate quantitative analysis cannot be achieved, because the precipitates of inorganic salts in the urine sample are not completely dissolved; and that membrane proteins present in the urine containing membrane components cannot be quantitated.

Patent Document 4: Japanese Unexamined Patent Application Publication No. 2000-352565

Patent Document 5 discloses an analytical reagent for analyzing formed elements in the urine, comprising a buffer for keeping the pH in the range of 5.0 to 9.0 and a chelating agent. The technique has the problems that the components of the urine supernatant or the whole urine cannot be quantitated, as it is an analytical reagent for analyzing formed elements in the urine, and that almost neat urine samples cannot be treated.

Patent Document 5: Japanese Unexamined Patent Application Publication No. 8-170960

Patent Document 6 describes that the urine sample is treated with a surfactant during the quantitation of urinary podocalyxin. The technique has problems that accurate quantitative analysis cannot be achieved because the urine pH is not completely compensated or homogenized; and that accurate quantitative analysis cannot be carried out because the precipitates of inorganic salts in the urine sample are not completely dissolved.

Patent Document 6: International Publication No. WO 2002/037099, brochure

DISCLOSURE OF INVENTION

Problems to be Solved by the Invention

In view of the above-described problems, it is required to develop a urine pretreatment agent, a urine pretreatment method, and a urinary protein quantitation method which reduce or cancel the influences of urine pH variations, cancel the influences of precipitates of urinary inorganic salts, and solubilize membrane proteins, thereby achieving stable immunological detection of urinary proteins in an almost neat urine sample without extensively diluting the neat urine.

Means for Solving the Problem

The present invention provides a urine pretreatment agent for urinary protein quantitation comprising a buffer, a chelating agent, and a surfactant.

In the urine pretreatment agent for urinary protein quantitation of the present invention, the buffer may be a Good's buffer.

The urine pretreatment agent for urinary protein quantitation of the present invention may further comprise at least one acid selected from the group consisting of acetic acid, phosphoric acid, citric acid, boric acid, and tartaric acid.

In the urine pretreatment agent for urinary protein quantitation of the present invention, the surfactant may be a polyalkylene oxide derivative.

The HLB value of the surfactant may be from 10 to 18.

The present invention provides a urine pretreatment method comprising a step of; mixing 10 to 1000 parts by mass of the urine pretreatment agent of the present invention to 5 with 100 parts by mass of urine.

The present invention provides a urinary protein quantitation method comprising steps of; mixing 10 to 1000 parts by mass of the urine pretreatment agent of the present invention with 100 parts by mass of urine; and then measuring the protein concentration.

The urinary protein quantitation method of the present invention may be a urinary podocalyxin quantitation method.

The urinary protein quantitation method of the present invention may be a urinary megalin quantitation method.

Advantageous Effect of the Invention

The urine pretreatment agent for urinary protein quantitation, urine pretreatment method, and urinary protein quantitation method of the present invention have advantages that they prevent the pH variations among urine samples, dissolve the precipitates of urinary inorganic salts, and solubilize membrane proteins, thereby allowing quantitative analysis of minor components in an almost neat urine sample.

Examples of the buffer described herein include, but not limited to, amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, carboxylates, phosphates, carbonates, and Good's buffers Examples of the Good's buffer described herein include, but not limited to, N-(2-Acetamido)-2-aminoethanesulfonic acid, N-(2-Acetamido)iminodiacetic acid, N,N-Bis(2-hydroxyethyl)-2-aminoethanesulfonic acid, N,N-Bis(2-hydroxyethyl)glycine, Bis(2-hydroxyethyl)iminotris(hydroxymethyl)methane, N-Cyclohexyl-3-aminopropanesulfonic acid, N-Cyclohexyl-2-aminoethanesulfonic acid, 3-[4-(2-Hydroxyethyl)-1-piperazinyl]propanesulfonic acid, 2-[4-(2-Hydroxyethyl)-1-piperazinyl]ethanesulfonic acid, 2-Hydroxy-3-[4-(2-hydroxyethyl)-1-piperazinyl]propanesulfonic acid, 2-Morpholinoethanesulfonic acid, 3-Morpholinopropanesulfonic acid, 2-Hydroxy-3-morpholinopropanesulfonic acid, piperazine-1,4-bis(2-ethanesulfonic acid), piperazine-1,4-bis(2-hydroxy-3-propanesulfonic acid, N-Tris(hydroxymethyl-3-aminopropanesulfonic acid, 2-Hydroxy-N-tris(hydroxymethyl)methyl-3-aminopropanesulfonic acid, N-Tris(hydroxymethyl)methyl-2-aminoethanesulfonic acid, N-[Tris(hydroxymethyl)methyl]glycine, 2-amino-2-hydroxymethylpropane-1,3-diol, Tris(hydroxymethyl)aminomethane. The buffer of the urine pretreatment agent of the present invention is preferably a Good's buffer, because it has a large buffer capacity, thus allowing efficient compensation and homogenization of urine pH.

The urine pretreatment agent of the present invention preferably contains a weak acid selected from the group consisting of acetic acid, phosphoric acid, citric acid, boric acid, and tartaric acid, thereby providing a wide buffer range. The loading of the weak acid is not particularly limited, but is preferably 90 parts by mass or less, and more preferably from 10 to 90 parts by mass in 100 parts by mass of the urine pretreatment agent. When the loading of the weak acid is within the above range, the pH value is readily maintained in an appropriate range.

Examples of the chelating agent described herein include, but not limited to, Ethylenediamine-N,N,N',N'-tetraacetic acid, O,O'-Bis(2-aminoethyl)ethyleneglycol-N,N,N',N'-tetraacetic acid, O,O'-Bis(2-aminophenyl)ethyleneglycol-N,N,N',N'-tetraacetic acid, N,N-Bis(2-hydroxyethyl)glycine, trans-1,2-Diaminocyclohexane-N,N,N',N'-tetraacetic acid, Diethyl enetriamine-N,N,N',N'',N''-pentaacetic acid, Ethylenediamine-N,N'-dipropionic acid, N-(2-Hydroxyethyl)iminodiacetic acid, Iminodiacetic acid, Nitrilotriacetic acid, Nitrilotris(methylphosphonic acid), N,N,N',N'-Tetrakis(2-pyridylmethyl)ethylenediamine, Triethylenetetramine-N,N,N',N'',N''',N''''-hexaacetic acid, Heparin, Sodium citrate, Sodium fluoride, acid citrate dextrose solution, Adenosine triphosphate. Preferred is ethylenediamine-N,N,N',N'-tetraacetate which achieves high masking effect on urinary calcium and urinary magnesium.

Examples of the surfactant described herein include, but not limited to, anionic, cationic, and nonionic surfactants. Among nonionic surfactants, preferred are polyethylene glycol surfactants derived from polyalkylene oxide, specifically polyethylene oxide mono(p-isooctylphenyl ether).

The HLB value (Hydrophile-Lipophile Balance value) of the surfactant of the present invention is not particularly limited, but preferably from 10 to 18, and more preferably from 11 to 15. When the HLB value is within the above range, the surfactant will not cause the separation of the urine sample into an aqueous phase and an oil phase, thus giving an accurate quantification value.

The proportions of the urine pretreatment agent of the present invention and urine pretreatment solution are not particularly limited, but preferably satisfy the following formulae (1) to (6) when the agent and solution are mixed with urine.

When the proportion of urine in the mixture of the urine and urine pretreatment agent is represented by X (%), the final concentration of the buffer contained in the mixture of the urine and urine pretreatment agent is represented by A (mM), and the concentration of the buffer in the urine pretreatment agent stock solution is represented by B (mM), they preferably satisfy the following formulae:

$$A \geq (20/9) \times X \quad (1)$$

$$B \geq 2000 \times X/9 \times (100-X) \quad (2)$$

When these formulae are satisfied, the urine pretreatment agent achieves the compensation and homogenization of the urine pH.

When the proportion of urine in the mixture of the urine and urine pretreatment agent is represented by X (%), the final concentration of the chelating agent contained in the mixture of the urine and urine pretreatment agent is represented by C (mM), and the concentration of the chelating agent in the urine pretreatment agent stock solution is represented by D (mM), they preferably satisfy the following formulae:

$$C \geq (2/9) \times X \quad (3)$$

$$D \geq 200 \times X/9 \times (100-X) \quad (4)$$

When these formulae are satisfied, the urine pretreatment agent dissolves the precipitates of urinary inorganic salts.

When the proportion of urine in the mixture of the urine and urine pretreatment agent is represented by X (%), the final concentration of the surfactant contained in the mixture of the urine and urine pretreatment agent is represented by E (%), and the concentration of the surfactant in the urine pretreatment agent stock solution is represented by F (%), they preferably satisfy the following formulae:

$$E \geq 0.2 \quad (5)$$

$$F \geq 20/(100-X) \quad (6)$$

When these formulae are satisfied, the urine pretreatment agent solubilizes membrane proteins bearing membrane components in the urine, and exhibits blocking effect by itself without the help of a protein blocking agent.

The proportion of the urine pretreatment agent preferably satisfies all the formulae (1) to (6). When these formulae are satisfied, accurate quantitative analysis of trace amounts of urinary analytes is achieved using the urine pretreatment agent.

The urine pretreatment agent of the present invention may contain additives such as a preservative and an antiseptic. Examples of the antiseptic include, but not limited to, sodium azide and isothiazolone-based antiseptics such as 5-chloro-2-methyl-4-isothiazoline-3-one and 2-methyl-4-isothiazoline-3-one.

The urine pretreatment agent of the present invention may contain an inhibitor. Examples of the inhibitor include, but not limited to, protein kinase inhibitors, G protein signal second messenger related inhibitors, calmodulin kinase related inhibitors, cyclin dependent kinase related inhibitors, MAP kinase signal related inhibitors, tyrosine kinase inhibitors, Wnt signal related inhibitors, Akt kinase signal related inhibitors, Notch signal inhibitors, protein phosphatase inhibitors, cytokine signal inhibitors, hormone related inhibitors, HDAC inhibitors, NFκB transcription factor inhibitors, inhibitors of transportation between nucleus and cytoplasm of protein and RNA, calcium signal channel inhibitors, nervous system related inhibitors, inhibitors of caspase, proteasome, and granzyme B etc., matrix metalloprotease inhibitors, COX, oxidative stress, and NO related inhibitors, apoptosis derivatives and inhibitors, neovascularization inhibitors, cytoskeleton and cell division inhibitors, telomerase inhibitors, sugar processing inhibitors, anticancer drugs, DNA polymerase inhibitors, RNA polymerase inhibitors, protein synthesis inhibitors, deoxyribonuclease inhibitors, and ribonuclease inhibitors.

The urine pretreatment agent of the present invention may be diluted with water or an organic solvent. The proportion of the urine pretreatment solution of the present invention is preferably about 10 to 1000 parts by mass in terms of the solid content with reference to 100 parts by mass of water.

The urinary protein quantitation method of the present invention is not particularly limited, and may include, for example, diluting a urine pretreatment agent with water etc. to make a urine pretreatment solution, adding the urine pretreatment solution to urine, and then determining the protein. The proportions of the urine and urine pretreatment agent are not particularly limited, but are preferably 5 to 100 parts by mass of the urine pretreatment agent with reference to 100 parts by mass of urine. When the proportions of the urine and urine pretreatment agent within the above range, the urine pretreatment agent is readily dissolved.

The quantitation of podocalyxin may use, for example, ELISA method of LA (Latex Agglutination-Turbidimetric Immunoassay) method. The quantitation of megalin may use, for example, CLEIA (Chemiluminescent Enzyme Immunoassay) method or META (Microparticle Enzyme Immunoassay) method. These methods achieves clarification without centrifugation, thus allowing reduction or elimination of blocking agents.

Urine is the end product of in vivo homeostasis, and thus is markedly influenced by physiological variations. Therefore, the quantitative value of urinary podocalyxin tends to have an error due to the individual difference variations caused during urine collection, daily difference variations, and daily variations. However, the problems of precipitates and phase separation causing the error can be resolved through the control of the loading of the buffer, chelating agent, and surfactant. As a result of this, stable quantitative values are obtained.

The pH value of the urine sample used for the quantitation of podocalyxin is not particularly limited, but is preferably from 5.5 to 7.0. If the pH is outside the range, the examination value may have an error.

The pH value of the urine sample used for the quantitation of megalin is not particularly limited, but is preferably from 7.0 to 9.0 in the alkaline range. If the pH in the acidic range, the examination value may have an error. There is no sample having a pH of more than 10.

The urine sample pretreatment method of the present invention is suitably used for the quantitation of urinary proteins such as podocalyxin and megalin. The proteins may be quantitated by, for example, an immunoassay method or a method including non-immunologically assaying the binding between substances.

Examples of the immunoassay method include, but not limited to, ELISA method, CLEIA (Chemiluminescent Enzyme Immunoassay) method, CLIA (Chemiluminescent Immunoassay) method, ECLIA (Electro Chemiluminescent Immunoassay) method, EIA method, FEIA (Fluorescence-Enzyme Immunoassay) method, IEP (Immunoelectrophoresis) method, IRMA (Immunoradiometric Assay) method, LA (Latex Agglutination-Turbidimetric Immunoassay) method, LIFA (Ligand-Mediated Immunofunctional Assay) method, LPIA (Latex Photometric Immunoassay) method, META (Microparticle Enzyme Immunoassay) method, PA (Particle Agglutination Test) method, PIA (Pulse Immunoassay) method, RIA (Radioimmunoassay) method, RPLA (Reversed Passive Latex Agglutination Test) method, SRID (Single Radial Immunodiffusion) method, TIA (Turbidimetric Immunoassay) method, immunochromatography method, immunoblotting method, Western blotting method, gold colloid immunoassay method, and nepherometry.

Examples of the method including non-immunologically assaying the binding between substances include, but not limited to, SBPA (Sandwich Binding Protein Assay) method, RRA (Radio Receptor Assay) method, and CPBA (Competitive Protein Binding Assay) method. Among these quantitation methods, preferred are ELISA method and immunochromatography method.

BEST MODE FOR CARRYING OUT THE INVENTION

Figure 1:
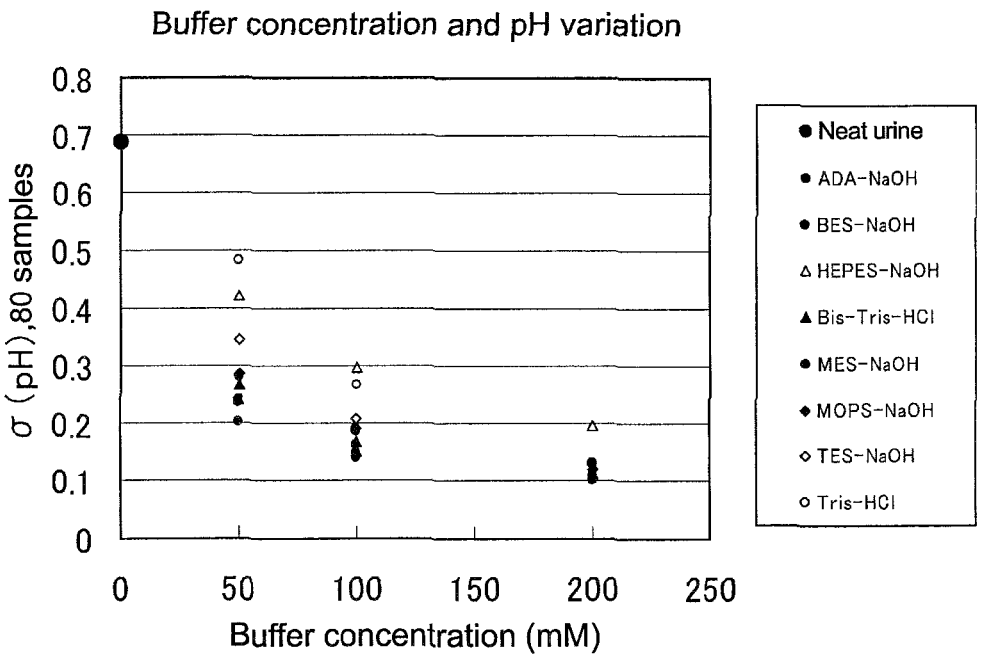
FIG. 1 is a graph showing the concentration-dependent effect of the buffer on the urine pH compensated using the urine pretreatment agent of the present invention.

The following examples represent the embodiments of the present invention, but will not limit the scope of the invention.

The reagents, materials, and apparatuses used in the following examples are described below.

Adjuvant: Freund's complete adjuvant and Freund's incomplete adjuvant (manufactured by DIFCO Laboratories)

TES: N-tris(hydroxymethyl)methyl-2-aminoethanesulfonic acid buffer (manufactured by Dojindo Laboratories)

EDTA: ethylenediamine-N,N,N',N'-tetraacetic acid chelating agent (manufactured by Dojindo Laboratories)

Triton X-100: a surfactant composed mainly of polyethylene glycol mono-p-isooctylphenyl ether, HLB value 12 (manufactured by Nacalai Tesque, Inc.)

Human podocalyxin: an extract from a glomerulus isolated from a human kidney (self-prepared)

Human podocalyxin aqueous solution: an aqueous solution (pH 7.3) containing 5 mg/L human podocalyxin, 140 mM NaCl, 2.7 mM KCl, 10 mM $Na_2HPO_4$, and 1.8 mM $KH_2PO_4$ Human megalin: an extract from human kidney renal cortex (self-prepared)

Human megalin aqueous solution: an aqueous solution (pH 7.3) containing 5 mg/L human podocalyxin, 140 mM NaCl, 2.7 mM KCl, 10 mM $Na_2HPO_4$, and 1.8 mM $KH_2PO_4$ PBS-T solution: 145 mM NaCl, 3.6 mM $Na_2HPO_4$, 1.4 mM $KH_2PO_4$, and 0.05% (v./v.) Tween 20

Blocking solution for antigen solid-phase plate: a solution containing 145 mM NaCl, 7.2 mM $Na_2HPO_4$, 2.8 mM $KH_2PO_4$, 1% (wt./v.) BSA (bovine serum albumin), and 5% (wt./v.) lactose TMB solution: an aqueous solution containing TMB (3,3',5,5'-tetramethylbenzidine), 300 mM, TMB One-Step Substrate System (manufactured by DAKO)

Enzyme labeled antibody diluent: a solution containing 145 mM NaCl, 3.6 mM $Na_2HPO_4$, 1.4 mM $KH_2PO_4$, 0.05% (v./v.) Tween 20, and 0.5% (wt./v.) BSA Sodium phosphate buffer solution: an aqueous solution (pH 7.0, commercial product) containing 20 mM sodium phosphate 1 mM acetic acid buffer solution: an aqueous solution (pH 4.0, commercial product) containing 1 mM sodium acetate 0.5 M carbonate buffer solution: a solution (pH 9.6, commercial product) containing 120 mM $Na_2CO_3$ and 380 mM $NaHCO_3$ 10 mM carbonate buffer solution: an aqueous solution (pH 9.6, commercial product) containing 2.4 mM $Na_2CO_3$ and 7.6 mM $NaHCO_3$ 1M Tris buffer solution: an aqueous solution (pH 9.0, commercial product) containing Tris (hydroxymethyl)aminomethane-HCl Labeled antibody suspension solution: a solution (pH 7.6, commercial product) containing 100 mM Tris, 145 mM NaCl, and 1% (v./v.) BSA Labeled antibody preservation solution: a solution (commercial product) containing 2.8 mM $KH_2PO_4$, 7.2 mM $Na_2HPO_4$, 145 mM NaCl, 1% (wt./v.) BSA, 0.02% (v./v.) phenol, and 40% (wt./v.) D-sorbitol HRP: peroxidase from horseradish Type VI (manufactured by Sigma)

Blocking solution for antibody solid-phase plate: an aqueous solution (commercial product) containing 86 mM NaCl, 100 mM Tris, 0.5% (wt./v.) BSA, and 0.05% (v./v.) Tween 20

Blocking solution for antigen solid-phase plate: 145 mM NaCl, 7.2 mM $Na_2HPO_4$, 2.8 mM $KH_2PO_4$, 1% (wt./v.) BSA, and 5% (wt./v.) lactose Reaction stop solution: a 313 mM $H_2SO_4$ solution Microtiter plate: Nunc-Immuno (Trademark) Module F8 Maxisorp (Trademark) Surface plate (manufactured by Nalge Nunc International)

Protein G column: HiTrap Protein G HP, 5 mL (manufactured by Amersham BioSciences).

(Samples)

Randomly chosen 80 urine samples collected in physical examinations were used. The samples are composed of 40 male urine samples and 40 female urine samples.

(Buffer)

The following reagents were used as buffers.

ADA-NaOH
BES-NaOH
BES-NaOH
HEPES-NaOH
MES-NaOH
MOPS-NaOH
TES-NaOH
Tris-HCl

The abbreviations are as follows.

ADA: N-(2-Acetamido)iminodiacetic acid

BES: N,N-Bis(2-hydroxyethyl)-2-aminoethanesulfonic acid

HEPES: 2-[4-(2-hydroxyethyl)-1-piperazinyl]ethanesulfonic acid

MES: 2-Morpholinoethanesulfonic acid, monohydrate

MOPS: 3-Morpholinopropanesulfonic acid

TES: N-Tris(hydroxymethyl)methyl-2-aminoethanesulfonic acid

Bis-Tris: Bis-(2-hydroxyethyl)iminotris(hydroxymethyl)methane

Tris: Tris(hydroxymethyl)aminomethane

Example 1

Evaluation Method (1) Urine Pretreatment Agent and Preparation of Urine Pretreatment Agent 7.4 g of chelating agent (EDTA), 10.7 g of surfactant (Triton X-100), and a buffer listed in Table 1 were mixed to make a urine pretreatment agent, and the urine pretreatment agent was mixed with water to make 100 mL of urine pretreatment solution.

(2) Pretreatment of Urine Sample 90 parts by mass of a urine sample was mixed with 10 parts by mass of a urine pretreatment solution, which had been prepared in accordance with the formula in Table 1, and then the pH value of the sample was measured with a pH meter. The urine pH was measured using a compact pH meter (Twin pH) manufactured by Horiba, Ltd.

(Results)

Table 1 lists the maximum, minimum, and average pH, and the standard deviation of the 80 samples measured by the above method, and FIG. 1 shows a graph prepared by plotting the standard deviation of the 80 samples against the buffer concentration.

TABLE 1

| Sample No. | Buffer | Buffer concentration (mM) | pH value of 80 samples | | | | Remarks |
|---|---|---|---|---|---|---|---|
| | | | Minimum | Maximum | Average | Standard deviation σ | |
| 1 | Neat urine | 0 | 5.0 | 7.8 | 6.26 | 0.687 | Comparative example |
| 2 | ADA-NaOH | 50 | 5.8 | 6.8 | 6.33 | 0.241 | Example |
| 3 | ADA-NaOH | 100 | 6.0 | 6.7 | 6.38 | 0.148 | Example |
| 4 | ADA-NaOH | 200 | 6.2 | 6.7 | 6.43 | 0.101 | Example |
| 5 | BES-NaOH | 50 | 6.0 | 7.1 | 6.59 | 0.281 | Example |
| 6 | BES-NaOH | 100 | 6.1 | 7.0 | 6.68 | 0.191 | Example |
| 7 | BES-NaOH | 200 | 6.5 | 7.0 | 6.75 | 0.110 | Example |
| 8 | Bis-Tris-HCl | 50 | 5.9 | 6.9 | 6.42 | 0.242 | Example |
| 9 | Bis-Tris-HCl | 100 | 6.2 | 6.8 | 6.46 | 0.151 | Example |
| 10 | Bis-Tris-HCl | 200 | 6.2 | 6.7 | 6.47 | 0.110 | Example |
| 11 | MES-NaOH | 50 | 5.6 | 6.5 | 6.00 | 0.203 | Example |
| 12 | MES-NaOH | 100 | 5.6 | 6.3 | 5.97 | 0.141 | Example |
| 13 | MOPS-NaOH | 50 | 6.0 | 7.0 | 6.56 | 0.286 | Example |
| 14 | MOPS-NaOH | 100 | 6.2 | 7.0 | 6.66 | 0.191 | Example |
| 15 | MOPS-NaOH | 200 | 6.5 | 7.0 | 6.75 | 0.121 | Example |
| 16 | TES-NaOH | 50 | 5.9 | 7.3 | 6.68 | 0.346 | Example |
| 17 | TES-NaOH | 100 | 6.3 | 7.2 | 6.85 | 0.208 | Example |
| 18 | TES-NaOH | 200 | 6.6 | 7.2 | 6.94 | 0.120 | Example |
| 19 | Tris-HCl | 50 | 6.2 | 8.2 | 7.43 | 0.483 | Example |
| 20 | Tris-HCl | 100 | 6.9 | 8.2 | 7.78 | 0.268 | Example |
| 21 | Tris-HCl | 200 | 7.5 | 8.2 | 7.93 | 0.132 | Example |

The results shown in Table 1 and FIG. 1 indicate that the pH control effect was markedly achieved when the buffer concentration was 200 mM or more in the pretreated urine sample.

Example 2

The aim of Example 2 is to apply a urine sample pretreatment solution composition and a urine sample pretreatment method using the same to a human urinary podocalyxin detection system using ELISA method.

Method (1) Production of Anti-Human Podocalyxin Mouse Monoclonal Antibody

50 μg of human podocalyxin was injected into mouse peritoneum several times together with an adjuvant, and the increase in serum titer was confirmed. Three days after intravenous booster injection, the spleen was taken out, and the spleen cells thus obtained and the mouse myeloma cells were fused in the proportions of 10:1 in terms of the cell count in the presence of polyethylene glycol 3500, thus producing hybridoma cells.

The hybridoma cells were cultured in a 5% $CO_2$ atmosphere at 37° C. for 1 week, and the presence or absence of the anti-human podocalyxin antibody in the culture supernatant was examined. Hybridoma cells in positive wells which exhibited antibody production were diluted by a limiting dilution method, cultured for 2 weeks, and the presence or absence of anti-human podocalyxin antibody in the culture supernatant was examined by EIA method using a human podocalyxin solid-phase microtiter plate, in the same manner as described above. The cells in the positive wells were subjected to limiting dilution again, and cultured in the same manner as described above. At this point, the cells producing the anti-human podocalyxin antibody were cultured in a flask, a portion of the culture was suspended in fetal calf serum (FCS) containing 10% dimethylsulfoxide (DMSO) to give a concentration of $5 \times 10^6$ cells/mL, and stored in liquid nitrogen.

Subsequently, the supernatant in each well was tested for the reactivity of the antibody produced in the culture supernatant against human podocalyxin. Firstly, the human podocalyxin aqueous solution was added to the wells of the microtiter plate at the rate of 100 μL/well, and human podocalyxin was allowed to adsorb to the microtiter plate at the rate of 500 ng/well at 4° C. for 12 hours, thereby the antigen to be solid-phased. After a lapse of 12 hours, the human podocalyxin aqueous solution was removed from the wells by decantation. A PBS-T solution was added to the wells at the rate of 200 μL/well, and removed by decantation, thereby washing off the excessive portions of human podocalyxin which did not adsorb to the wells to be solid-phased. The washing process was carried out twice.

Thereafter, a blocking solution for the antigen solid-phase plate was added to the wells at the rate of 200 μL/well, and the wells of the human podocalyxin solid-phased microtiter plate were subjected to blocking at 4° C. for 12 hours. After a lapse of 12 hours, the human podocalyxin solid-phased microtiter plate after completion of blocking was stored with the temperature kept at 4° C. The human podocalyxin solid-phased microtiter plate after completion of blocking was used to test the reactivity of the antibody in the culture supernatant. The hybridoma culture supernatant was added to the wells of the human podocalyxin solid-phased microtiter plate at the rate of 100 μL/well, and warmed at 37° C. for 1 hour. Thereafter, the culture supernatant was removed from the wells by decantation. PBS-T was added to the wells at the rate of 200 μL/well, and the PBS-T was removed by decantation, thereby washing the wells. The washing process was carried out three times.

Thereafter, peroxidase-conjugated goat anti-mouse immunoglobulin (manufactured by DAKO) was added to the wells at the rate of 100 μL/well (2000-fold dilution: 0.55 μg/mL), and warmed at 37° C. for 1 hour. The enzyme-labeled antibody was diluted with an enzyme-labeled antibody diluent. Thereafter, the enzyme-labeled antibody in the wells was removed by decantation, PBS-T was added at the rate of 200 μL/well, and removed by decantation, thereby washing the wells. The washing process was carried out three times.

Thereafter, a TMB solution as a peroxidase reactant substrate solution was added to the wells at the rate of 100 μL/well, and allowed to stand at 25° C. for 30 minutes. Immediately after that, a reaction stop solution (313 mM $H_2SO_4$ solution) was added to the substrate reactant solution in the wells at the rate of 100 μL/well, thereby stopping the enzyme reaction in the wells. Thereafter, the absorbance of the wells was measured. The result of subtracting the absorbance at 630 nm from the absorbance 450 nm was used as the index of reactivity evaluation.

As a result of this, the hybridoma cells producing culture supernatant exhibiting strong reactivity against the solid-phased human podocalyxin were selected. The antibody class and subclass of the immunoglobulin in the culture supernatant were examined for each clone of the hybridoma cells using immunoglobulin Typing Kit, Mouse (manufactured by Wako Pure Chemical Industries, Ltd.). On the basis of the results, the clone cells producing IgG class were chosen from the single clone cell library thus obtained, proliferated in a 25-mL flask, and further proliferated in a 75-mL flask. The cells were injected into pristane-treatment mouse peritoneum, and the ascites was collected.

(2) Purification of Anti-Human Podocalyxin-Mouse Monoclonal Antibody IgG

Mouse ascites (10 mL) and a turbid serum treating agent (FRIGEN (registered trademark) II, manufactured by Kyowa Pure Chemical Co., Ltd.) were mixed at the rate of 1.5 volumes of ascites to 1 volume of FRIGEN (registered trademark) II, the mixture was shaken for 1 to 2 minutes, thereby degreasing the ascites. Centrifugation was carried out using a centrifugal machine at 1930×g for 10 minutes, thus 10 mL of clarified ascites centrifugated supernatant was obtained.

The ascites centrifugated supernatant (10 mL) was subjected to ammonium sulfate fractionation for 1 hour in an ice bath (final concentration: 50% saturated ammonium sulfate), and the precipitated immunoglobulin fraction was suspended and dissolved in PBS. The ammonium sulfate fractionation was carried out twice, thereby collecting a rough IgG fraction from the ascites.

The immunoglobulin rough fraction (10 mL) thus obtained was mixed with an isometric sodium phosphate buffer solution, and subjected to affinity purification using a protein G column. The sample was allowed to adsorb to the protein G column, and then a sodium phosphate buffer solution was passed through the protein G column, thereby washing off impurities other than IgG from the sample. Thereafter, the IgG adsorbed to the protein G column was eluted with a 0.1 M glycine-HCl (pH 2.7) aqueous solution. The eluate containing IgG was neutralized with a 1 M Tris buffer solution, and purified by dialysis twice of 500 volumes of PBS with reference to the volume of the eluate from affinity purification at 4° C. for each 6 hours. The dialysis was achieved using a dialysis cellulose tube (manufactured by Viskase Companies). The IgG eluted fraction thus dialyzed was used as a purified product of the anti-human podocalyxin monoclonal antibody. The anti-human podocalyxin monoclonal antibody was stored at 4° C.

The IgG was purified using BioLogic LP system (manufactured by Bio Rad Laboratories) connected to the protein G column, wherein the flow rate was adjusted to 1 mL/minute.

(3) Production of Anti-Human Podocalyxin Monoclonal Antibody Solid-Phased Microtiter Plate The purified anti-human podocalyxin monoclonal antibody was dissolved in PBS (pH 7.3) to give a final concentration of 7 μg/mL. The purified anti-human podocalyxin monoclonal antibody/PBS solution was added to the wells of the microtiter plate at the rate of 100 μL/well, and the anti-human podocalyxin monoclonal antibody was made to be solid-phased on the microtiter plate at 4° C. for 12 hours. After a lapse of 12 hours, the anti-human podocalyxin monoclonal antibody/PBS solution was removed from the wells by decantation, PBS-T was added to the wells at the rate of 200 μL/well, and removed by decantation, thereby washing off the excessive portions of anti-human podocalyxin monoclonal antibody which did not adsorb to the wells to be solid-phased. The washing process was carried out twice. Thereafter, a blocking solution for the antibodies solid-phased plate was added at the rate of 200 μL/well, and the wells of the microtiter plate solidified with the anti-human podocalyxin monoclonal antibody were subjected to blocking at 4° C. for 12 hours. After a lapse of 12 hours, the microtiter plate was stored at 4° C.

(4) Production of HRP-Labeled Anti-Human Podocalyxin Monoclonal Antibody

Horseradish peroxidase (HRP) was dissolved in pure water to give a concentration of 4 mg/mL, thus making a HRP aqueous solution. 500 μL (2 mg) of the HRP solution was mixed with 100 μL of 100 mM sodium metaperiodate solution, and the mixture was stirred for 20 minutes at room temperature. The HRP solution was dialyzed twice of 500 volumes of 1 mM acetic acid buffer solution at 4° C. each for 6 hours. The dialysis was achieved using a dialysis cellulose tube (manufactured by Viskase Companies). Subsequently, the anti-human podocalyxin monoclonal antibody was dissolved in 10 mM carbonate buffer solution to give a concentration of 8 mg/mL. 500 μL (2 mg) of the HRP solution was mixed with ⅓ volumes of 0.5M carbonate buffer solution, and further mixed with 500 μL (4 mg) of the anti-human podocalyxin monoclonal antibody/10 mM carbonate buffer solution, and the mixture was stirred at room temperature for 2 hours. Thereafter, a sodium borohydride solution (50 μL) was added to give a concentration of 4 mg/mL, and stirred in an ice water bath for 2 hours. The solution was subjected to ammonium sulfate fractionation (final concentration: 50% saturated ammonium sulfate) in an ice bath for 1 hour, the precipitated fraction was suspended and dissolved in 1 mL of labeled antibody suspension. The ammonium sulfate fractionation was carried out twice, and ¾ volumes of the labeled antibody preservation solution was added to the whole volume of the labeled antibody suspension, thus obtaining a HRP-labeled anti-human podocalyxin monoclonal antibody stock solution.

(5) Quantitation of Human Urinary Podocalyxin

The microtiter plate with the solid-phased anti-human podocalyxin monoclonal antibody and the HRP-labeled anti-human podocalyxin monoclonal antibody were used to quantitate human urinary podocalyxin. Firstly, 90 μL of the urine sample was mixed with 10 μL of an aqueous solution (pH 7.0) containing 2 M TES, 0.2 M EDTA, and 2% (v./v.) Triton X-100, and 100 μL of the mixture was added to a well of the microtiter plate solidified with the anti-human podocalyxin monoclonal antibody. The microtiter plate was allowed to stand at 37° C. for 1 hour. The urine sample solution was removed from the well by decantation, and PBS-T was added to the well at the rate of 200 μL/well, and removed by decantation, thereby washing the well. The washing process was carried out three times.

Thereafter, the stock solution prepared in the section (4) of Example 2 was diluted 10,000 fold with a labeled antibody diluent, and the HRP-labeled anti-human podocalyxin monoclonal antibody solution thus obtained was added at the rate of 100 μL/well. After the solution was allowed to stand at 37° C. for 1 hour, the HRP-labeled antibody solution was removed by decantation. PBS-T was added to the well at the rate of 200

μL/well, and removed by decantation, thereby washing the well. The washing process was carried out three times. Subsequently, a TMB solution as a peroxidase enzyme reactant solution was added to the well at the rate of 100 μL/well, and allowed to stand at 25° C. for 30 minutes. Immediately after that, a reaction stop solution was added to the substrate reactant solution in the well at the rate of 100 μL/well to stop the enzyme reaction in the well, thus making a sample for absorption measurement. The 450 nm and 630 nm absorbances of the sample for absorption measurement were measured, and the result of subtracting the absorbance at 630 nm from the absorbance at 450 nm was used as the index of human urinary podocalyxin quantitation. The human podocalyxin used as a immunizing antigen in the production of the anti-human podocalyxin monoclonal antibody was used as the reference standard for preparing a calibration curve. The actual urinary podocalyxin concentration was calculated from the calibration curve.

Figure 2:
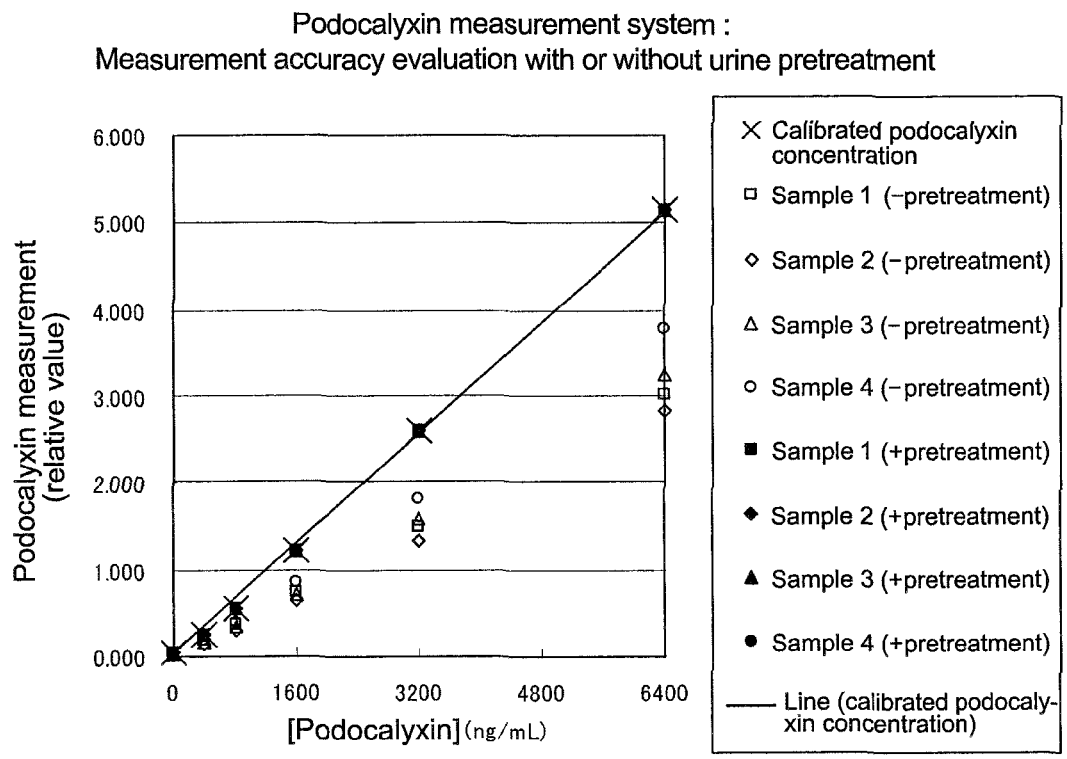
FIG. 2 is a graph showing the improvements in the accuracy of the urinary podocalyxin measurement system in the presence of the urine pretreatment agent of the present invention.

Accurate quantitation and detection of human urinary podocalyxin were not achieved until the urine sample pretreatment solution composition and the urine sample pretreatment method using the same of the present invention were applied to the quantitation of human urinary podocalyxin. The effects of the present invention were verified using urine of an normal subject which has been proved to be free of podocalyxin. A podocalyxin antigen standard was added to the urine, and errors of quantitation of podocalyxin in the urine samples and the effects of the present invention were confirmed. The results are shown in Table 2 and FIG. 2.

TABLE 2

| [Podocalyxin] (ng/mL) | Standard calibrated value | Sample 1 | | Sample 2 | | Sample 3 | | Sample 4 | | Remarks Pretreated or not Podocalyxin measurement (relative value) |
|---|---|---|---|---|---|---|---|---|---|---|
| | | Pre-treatment (−) | Pre-treatment (+) | Pre-treatment (−) | Pre-treatment (+) | Pre-treatment (−) | Pre-treatment (+) | Pre-treatment (−) | Pre-treatment (+) | |
| | | | | | O.D.(450 nm-630 nm) | | | | | |
| 6400 | 5.146 | 3.027 | 5.146 | 2.837 | 5.145 | 3.256 | 5.146 | 3.791 | 5.136 | Example |
| 3200 | 2.619 | 1.503 | 2.619 | 1.348 | 2.618 | 1.585 | 2.619 | 1.813 | 2.614 | Example |
| 1600 | 1.224 | 0.737 | 1.224 | 0.649 | 1.223 | 0.711 | 1.216 | 0.852 | 1.223 | Example |
| 800 | 0.549 | 0.359 | 0.549 | 0.309 | 0.549 | 0.338 | 0.549 | 0.393 | 0.548 | Example |
| 400 | 0.253 | 0.179 | 0.253 | 0.150 | 0.253 | 0.161 | 0.253 | 0.188 | 0.252 | Example |
| 0 | 0.036 | 0.035 | 0.036 | 0.035 | 0.036 | 0.035 | 0.036 | 0.035 | 0.036 | Example |
| | | | | | Divergence from standard value (%) | | | | | |
| 6400 | — | 64 | 0 | 67 | 1 | 61 | 1 | 51 | 4 | |
| 3200 | — | 65 | 0 | 70 | 2 | 63 | 1 | 55 | 5 | |
| 1600 | — | 63 | 2 | 69 | 2 | 65 | 8 | 55 | 2 | |
| 800 | — | 59 | 1 | 66 | 2 | 62 | 1 | 53 | 3 | |
| 400 | — | 54 | 0 | 64 | 4 | 60 | 2 | 51 | 7 | |
| 0 | — | 15 | 3 | 18 | 1 | 20 | 2 | 13 | 0 | |

Example 3

The aim of Example 3 is to evaluate the pH-dependent reactivity of the human urinary podocalyxin detection system using ELISA method.

The urinary podocalyxin measurement system established in Example 2 was evaluated for its pH-dependent reactivity. In order to evaluate the pH dependence, in place of urine samples, pH reactivity test solutions were prepared, the solutions containing different six buffer solutions having different pH values composed of 50 mM MES-NaOH (pH 5.5, 6.0, 6.5, or 7.0) or 50 mM Tris-HCl (pH 8.0 or 8.5), and 0.2% (v./v.) Triton X-100, and 20 mM EDTA. A pH reactivity test solution spiked with a human podocalyxin antigen was used in place of a urine sample, and tested for the pH dependence in the urinary megalin measurement system.

TABLE 3

| [Podocalyxin] (ng/mL) | pH 5.5 | pH 6.0 | pH 6.5 | pH 7.0 | pH 8.0 | pH 8.5 | Remarks Podocalyxin measurement (relative value) |
|---|---|---|---|---|---|---|---|
| | | | O.D.(450 nm-630 nm) | | | | |
| 3200 | 3.368 | 3.245 | 3.449 | 1.872 | 1.027 | 0.874 | Example |
| 1600 | 1.684 | 1.541 | 1.660 | 0.711 | 0.410 | 0.370 | Example |
| 800 | 0.690 | 0.597 | 0.641 | 0.285 | 0.171 | 0.168 | Example |
| 400 | 0.278 | 0.229 | 0.248 | 0.110 | 0.090 | 0.083 | Example |

TABLE 3-continued

| [Podocalyxin] (ng/mL) | pH 5.5 | pH 6.0 | pH 6.5 | pH 7.0 | pH 8.0 | pH 8.5 | Remarks Podocalyxin measurement (relative value) |
| --- | --- | --- | --- | --- | --- | --- | --- |
| 200 | 0.105 | 0.091 | 0.098 | 0.057 | 0.049 | 0.050 | Example |
| 100 | 0.050 | 0.044 | 0.047 | 0.035 | 0.032 | 0.034 | Example |
| 50 | 0.033 | 0.031 | 0.032 | 0.028 | 0.027 | 0.025 | Example |
| 0 | 0.022 | 0.022 | 0.021 | 0.026 | 0.023 | 0.021 | Example |

Figure 3:
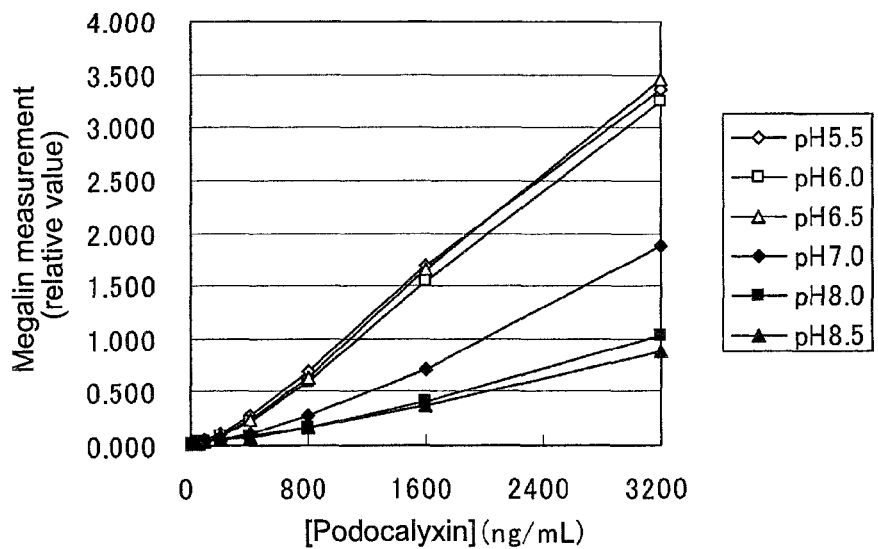
FIG. 3 is a graph showing the pH dependence of the urinary podocalyxin measurement system.

As shown in Table 3 and FIG. 3, the reactivity was lower in the higher pH range, and the reactivity of the urinary podocalyxin measurement system increased as the decrease in pH. The present invention is intended to provide a urine sample pretreatment solution composition and a urine sample pretreatment method using the same; Through the use of them, influences of factors causing measurement errors on the detection and measurement systems are canceled, which allows the tests and measurements of almost neat urine samples. The above-described results indicate the possibility of simple, short-time, and accurate quantitation of urine samples in clinical tests, and strongly supports the effects of the present invention.

Example 4

The aim of Example 4 is to apply the urine sample pretreatment solution composition and the urine sample pretreatment method using the same to a human urinary megalin detection system using ELISA method.

Method (1) Production of Anti-Human Megalin-Mouse Monoclonal Antibody

50 µg of human megalin was injected into mouse peritoneum several times together with an adjuvant, and the increase in serum titer was confirmed. Three days after intravenous booster injection, the spleen was taken out, and the spleen cells thus obtained and the mouse myeloma cells were fused in the proportions of 10:1 in terms of the cell count in the presence of polyethylene glycol 3500, thus producing hybridoma cells.

The hybridoma cells were cultured in a 5% $CO_2$ atmosphere at 37° C. for 1 week, and the presence or absence of the anti-human megalin antibody in the culture supernatant was examined. Hybridoma cells in positive wells which exhibited antibody production were diluted by a limiting dilution method, cultured for 2 weeks, and the presence or absence of anti-human megalin antibody in the culture supernatant was examined by EIA method using a human megalin solid-phased microtiter plate, in the same manner as described above. Thereafter, the cells in the positive wells were subjected to limiting dilution again, and cultured in the same manner as described above. At this point, the cells producing the anti-human megalin antibody were cultured in a flask, a portion of the culture was suspended in fetal calf serum (FCS) containing 10% dimethylsulfoxide (DMSO) to give a concentration of $5 \times 10^6$ cells/mL, and stored in liquid nitrogen.

Subsequently, the supernatant in each well was tested for the reactivity of the antibody produced in the culture supernatant against human megalin. 0.05 mg of human megalin was dissolved in 10 mL of a solution containing 140 mM NaCl, 2.7 mM KCl, 10 mM $Na_2HPO_4$ and 1.8 mM $KH_2PO_4$ (pH 7.3 or less, hereinafter abbreviated as "PBS, pH 7.3").

The human megalin/PBS, pH 7.3 aqueous solution was added to the wells of the microtiter plate at the rate of 100 µL/well, thereby the human megalin to be solid phased on the microtiter plate at 4° C. for 12 hours at the rate of 3 pmol/well. After a lapse of 12 hours, the human megalin/PBS, pH 7.3 solution in the wells was removed by decantation, and a PBS-T solution was added to the wells at the rate of 200 µL/well, and removed by decantation, thereby washing off the excessive portions of human megalin which did not adsorb to the wells and solidify. The washing process was carried out twice. Thereafter, a blocking solution for the antigen solid-phased plate was added to the wells at the rate of 200 µL/well, and the wells of the human megalin solid-phased microtiter plate were subjected to blocking at 4° C. for 12 hours. After a lapse of 12 hours, the human megalin solid-phased microtiter plate after completion of blocking was stored with the temperature kept at 4° C.

The human megalin solid-phased microtiter plate after completion of blocking was used to test the reactivity of the antibody in the culture supernatant. The hybridoma culture supernatant was added to the wells of the human megalin solid-phased microtiter plate at the rate of 100 µL/well, and warmed at 37° C. for 1 hour. Thereafter, the culture supernatant was removed by decantation from the wells. PBS-T was added to the wells at the rate of 200 µL/well, and the PBS-T was removed by decantation, thereby washing the wells. The washing process was carried out three times.

Thereafter, peroxidase-conjugated goat anti-mouse immunoglobulin (manufactured by DAKO) was added to the wells at the rate of 100 µL/well (2000-fold dilution: 0.55 µg/mL), and warmed at 37° C. for 1 hour. The enzyme-labeled antibody was diluted with an enzyme-labeled antibody diluent. Thereafter, the enzyme-labeled antibody in the wells was removed by decantation, PBS-T was added at the rate of 200 µL/well, and removed by decantation, thereby washing the wells. The washing process was carried out three times. Thereafter, a TMB solution as a peroxidase enzyme reactant substrate solution was added to the wells at the rate of 100 µL/well, and allowed to stand at 25° C. for 30 minutes. Immediately after that, a reaction stop solution was added to the reactant solution in the wells at the rate of 100 µL/well, thereby stopping the enzyme reaction in the wells. Thereafter, the absorbance of the wells was measured. The result of subtracting the absorbance at 630 nm from the absorbance 450 nm was used as the index of reactivity evaluation.

As a result of this, the hybridoma cells producing culture supernatant exhibiting strong reactivity against the solid-phased human megalin were selected. The antibody class and subclass of the immunoglobulin in the culture supernatant were examined for each clone of the hybridoma cells using immunoglobulin Typing Kit, Mouse (manufactured by Wako Pure Chemical Industries, Ltd.). On the basis of the results, the clone cells producing IgG class were chosen from the single clone cell library thus obtained, proliferated in a 25-mL flask, and further proliferated in a 75-mL flask. The cells were injected into pristane-treatment mouse peritoneum, and the ascites was collected.

(2) Purification of Anti-Human Megalin-Mouse Monoclonal Antibody IgG

The ascites (10 mL) thus obtained and a turbid serum treating agent (FRIGEN (registered trademark) II, manufactured by Kyowa Pure Chemical Co., Ltd.) were mixed at the rate of 1.5 volumes of ascites to 1 volume of FRIGEN (registered trademark) II, the mixture was shaken for 1 to 2 minutes, thereby degreasing the ascites. Centrifugation was carried out using a centrifugal machine at 1930×g for 10 minutes, thus 10 mL of clarified ascites supernatant was obtained. The ascites supernatant (10 mL) was subjected to ammonium sulfate fractionation for 1 hour in an ice bath (final concentration: 50% saturated ammonium sulfate), and the precipitated immunoglobulin fraction was suspended and dissolved in PBS. The ammonium sulfate fractionation was carried out twice, thereby collecting a rough IgG fraction from the ascites. The immunoglobulin rough fraction (10 mL) thus obtained was mixed with an equal mass of sodium phosphate buffer solution, and subjected to affinity purification using a protein G column (HiTrap Protein G HP, 5 mL: manufactured by Amersham BioSciences). The sample was allowed to adsorb to the protein G column, and then 50 mL of 20 mM sodium phosphate buffer solution was passed through the protein G column, thereby washing off impurities other than IgG from the sample. Thereafter, the IgG affinity-adsorbed to the protein G column was eluted with a 0.1 M glycine-HCl (pH 2.7) aqueous solution, and the eluted fraction immediately after the elution from the column was neutralized with a 1 M Tris buffer solution, and collected. After the neutralization, the affinity-purified product was dialyzed twice of 500 volumes of PBS at 4° C. for each 6 hours. The dialysis membrane used for the dialysis was a dialysis cellulose tube (manufactured by Viskase Companies). The IgG elution fraction thus obtained was used as a purified product of the anti-human megalin monoclonal antibody. The anti-human megalin monoclonal antibody was stored at 4° C. In the purification process, the above-described protein G column was connected to BioLogic LP System (Bio Rad Laboratories), and the flow rate was maintained at 1 mL/minute.

(3) Production of Anti-Human Megalin Monoclonal Antibody Solid-Phased Microtiter Plate The purified anti-human megalin monoclonal antibody was dissolved in a PBS aqueous solution (pH 7.3) to give a final concentration of 7 μg/mL. The anti-human megalin monoclonal antibody/PBS aqueous solution (pH 7.3) was added to the wells of a microtiter plate at the rate of 100 μL/well, and the anti-human megalin monoclonal antibody was made to be solid-phased on the microtiter plate at 4° C. for 12 hours. After a lapse of 12 hours, the anti-human megalin monoclonal antibody/PBS aqueous solution (pH 7.3) was removed from the wells by decantation. PBS-T was added to the wells at the rate of 200 μL/well, and removed by decantation, thereby washing off the excessive portions of the anti-human megalin monoclonal antibody which did not adsorb to the wells to be solid-phased. The washing process was carried out twice. Thereafter, a blocking solution for the antibody solid-phased plate was added at the rate of 200 μL/well, and the wells of the microtiter plate with the solid-phased anti-human megalin monoclonal antibody were subjected to blocking at 4° C. for 12 hours. After a lapse of 12 hours, the microtiter plate was stored at 4° C.

(4) Production of Peroxidase-Labeled Anti-Human Megalin Monoclonal Antibody

Horseradish peroxidase (hereinafter abbreviated as HRP) was dissolved in pure water to give a concentration of 4 mg/mL, thus making a HRP aqueous solution. 500 μμL (2 mg) of the HRP solution was mixed with 100 μL of 100 mM metaperiodic acid sodium solution, and the mixture was stirred for 20 minutes at room temperature. The HRP solution was dialyzed twice of 500 volumes of 1 mM acetic acid buffer solution at 4° C. each for 6 hours. The dialysis was achieved using a dialysis cellulose tube (manufactured by Viskase Companies). After the dialysis, the anti-human megalin monoclonal antibody was dissolved in 10 mM carbonate buffer solution to give a concentration of 8 mg/mL. 500 μL (2 mg) of the HRP solution was mixed with ⅓ volumes of 0.5 M carbonate buffer solution, and further mixed with 500 μL (4 mg) of the anti-human megalin monoclonal antibody/10 mM carbonate buffer solution, and the mixture was stirred at room temperature for 2 hours. Further, a sodium borohydride solution (50 μL) was added to give a concentration of 4 mg/mL, and stirred in an ice water bath for 2 hours. The solution was subjected to ammonium sulfate fractionation (final concentration: 50% saturated ammonium sulfate) in an ice bath for 1 hour, the precipitated fraction was suspended and dissolved in 1 mL of labeled antibody suspension. The ammonium sulfate fractionation was carried out twice, and ¾ volumes of the labeled antibody preservation solution was added to the whole volume of the labeled antibody suspension, thus obtaining a HRP-labeled anti-human megalin monoclonal antibody stock solution.

(5) Quantitation of Human Urinary Megalin

The microtiter plate with the solid-phased HRP-labeled anti-human megalin monoclonal antibody and the HRP-labeled anti-human megalin monoclonal antibody were used to quantitate human urinary megalin (hereinafter may be referred to as human megalin). Human megalin was quantitated as follows. 90 μL of the urine sample was mixed with 10 μL of an aqueous solution (pH 7.0) containing 2M TES, 0.2M EDTA, and 2% (v./v.) Triton X-100, and 100 μL of the mixture was added to a well of the microtiter plate with the solid-phased anti-human megalin monoclonal antibody. The microtiter plate was allowed to stand at 37° C. for 1 hour. The urine sample solution was removed from the well by decantation, and PBS-T was added to the well at the rate of 200 μL/well, and removed decantation, thereby washing the well. The washing process was carried out three times. Thereafter, the stock solution prepared in the section (4) of Example 4 was diluted 10,000 fold with a labeled antibody diluent, and the HRP-labeled anti-human megalin monoclonal antibody solution thus obtained was added at the rate of 100 μL/well. After the solution was allowed to stand at 37° C. for 1 hour, the HRP-labeled antibody solution was removed by decantation. PBS-T was added to the well at the rate of 200 μL/well, and removed by decantation, thereby washing the well. The washing process was carried out three times. Subsequently, a TMB solution as a peroxidase enzyme reactant substrate solution was added to the well at the rate of 100 μL/well, and allowed to stand at 25° C. for 30 minutes. A reaction stop solution was added to the reactant solution in the well at the rate of 100 μL/well to stop the enzyme reaction in the well, thus making a sample for measuring absorbance. Thereafter, the absorbance of the well was measured, and the result of subtracting the absorbance at 630 nm from the absorbance 450 nm was used as the index of the quantitation of human urinary megalin.

Human megalin, which had been used as an immunizing antigen in the production of the anti-human megalin monoclonal antibody, was used as the reference standard for preparing a calibration curve. A megalin antigen standard was added to urine of a normal subject which had been proved to be free of megalin, and errors of quantitation of megalin in the urine samples and the effects of the present invention were confirmed. When no urine sample pretreatment was carried out, the measurements markedly varied among the urine samples containing equal amounts of a antigen standard due to the differences (individual difference, daily difference), which results in the failure of quantitative evaluation.

Figure 4:
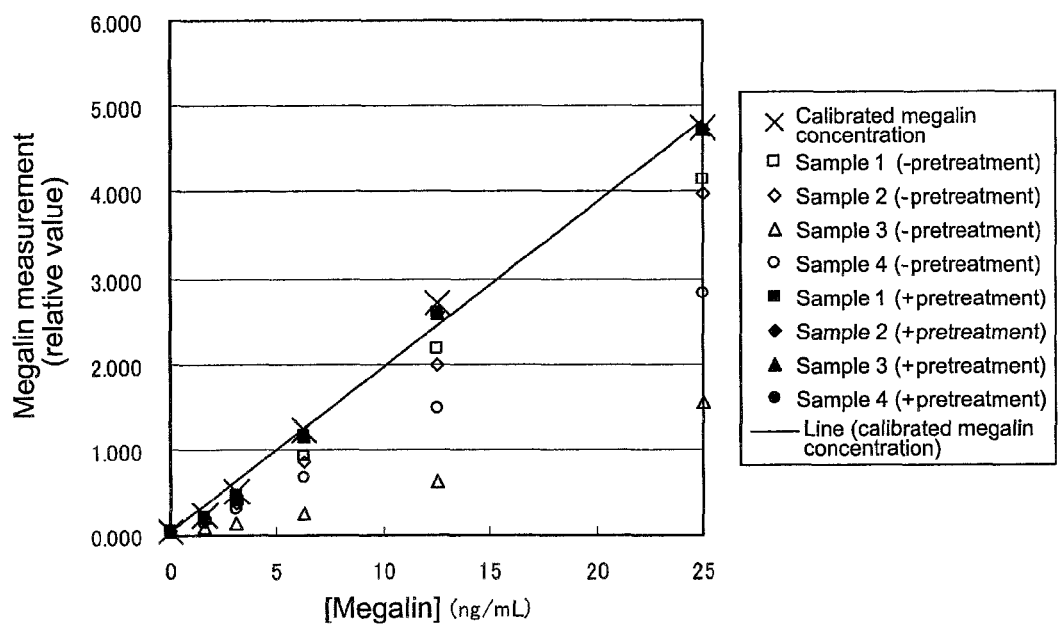
FIG. 4 is a graph showing the improvements in the accuracy of the urinary megalin measurement system in the presence of the urine pretreatment agent of the present invention.

This is likely due to negative factors such as the difference in the urine pH between samples, chaotropic effects of urinary magnesium and calcium, and deposition or accumulation of precipitates of urinary inorganic salts on the measurement system. Accurate quantitation and detection of human urinary megalin were not achieved until the urine sample pretreatment solution composition and the urine sample pretreatment method using the same of the present invention were applied to the quantitation of human urinary megalin. The effects of the present invention were verified using by adding urine of an normal subject which has been proved to be free of megalin. A megalin antigen standard was added to the urine, and errors of quantitation of megalin in the urine samples and the effects of the present invention were examined. The results are shown in Table 4 and FIG. 4.

ing measurement errors on the detection and measurement systems are canceled, which allows the tests and measurements of almost neat urine samples. The use of the method of the present invention has allowed simple, short-time, and accurate measurement of urine samples in clinical tests.

Example 5

The aim of Example 5 is to evaluate the pH dependence of the human urinary megalin detection system using ELISA method.

The pH-dependent reactivity of the urinary megalin measurement system shown in Example 4 was evaluated. The procedures are the same as described in Example 4. In order to evaluate the pH dependence, in place of urine samples, MES and Tris buffer solutions were used. Six buffer solutions containing 50 mM MES-NaOH (pH 5.5, pH 6.0, pH 6.5, or pH 7.0) or 50 mM Tris-HCl (pH 8.0 or 8.5) and having different pH values, and a pH reactivity test solution containing 1% (v./v.) Triton X-100 and 20 mM EDTA were prepared. A pH reactivity test solution spiked with a human megalin antigen was subjected to the urinary megalin measurement system in place of a urine sample, whereby the pH dependence was evaluated. As a result of this, as shown in Table 5

TABLE 4

| [Megalin] (ng/mL) | Standard calibrated value | Sample 1 | | Sample 2 | | Sample 3 | | Sample 4 | | Remarks Pretreated or not |
|---|---|---|---|---|---|---|---|---|---|---|
| | | Pre-treatment (−) | Pre-treatment (+) | Pre-treatment (−) | Pre-treatment (+) | Pre-treatment (−) | Pre-treatment (+) | Pre-treatment (−) | Pre-treatment (+) | Megalin measurement (relative value) |
| O.D.(450 nm-630 nm) | | | | | | | | | | |
| 25.00 | 4.740 | 4.156 | 4.713 | 3.977 | 4.737 | 1.547 | 4.718 | 2.822 | 4.731 | Example |
| 12.50 | 2.718 | 2.172 | 2.714 | 1.993 | 2.712 | 0.637 | 2.706 | 1.475 | 2.716 | Example |
| 6.25 | 1.223 | 0.926 | 1.221 | 0.846 | 1.218 | 0.252 | 1.212 | 0.677 | 1.222 | Example |
| 3.13 | 0.509 | 0.400 | 0.508 | 0.366 | 0.507 | 0.137 | 0.504 | 0.295 | 0.507 | Example |
| 1.56 | 0.231 | 0.185 | 0.230 | 0.179 | 0.230 | 0.083 | 0.229 | 0.139 | 0.230 | Example |
| 0.00 | 0.039 | 0.037 | 0.040 | 0.037 | 0.040 | 0.036 | 0.040 | 0.038 | 0.040 | Example |
| Divergence from standard value (%) | | | | | | | | | | |
| 25.00 | — | 35 | 8 | 40 | 3 | 82 | 7 | 64 | 5 | |
| 12.50 | — | 45 | 4 | 52 | 5 | 88 | 7 | 68 | 3 | |
| 6.25 | — | 49 | 5 | 56 | 6 | 89 | 10 | 67 | 3 | |
| 3.13 | — | 46 | 6 | 53 | 7 | 86 | 10 | 65 | 6 | |
| 1.56 | — | 45 | 6 | 47 | 7 | 80 | 7 | 63 | 7 | |
| 0.00 | — | 22 | 0 | 24 | 2 | 27 | 1 | 20 | 2 | |

Figure 5:
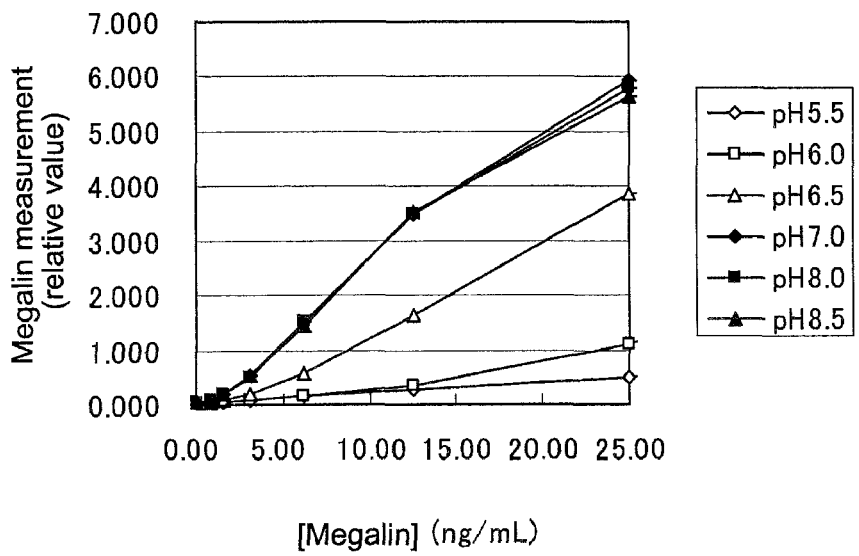
FIG. 5 is a graph showing the pH dependence of the urinary megalin measurement system.

Through the use of the urine sample pretreatment solution composition and the urine sample pretreatment method using the same of the present invention, influences of factors causing and FIG. 5, the reactivity was lower in the lower pH range, and the reactivity of the urinary megalin measurement system increased as the increase in the pH.

TABLE 5

| [Megalin] (ng/mL) | pH 5.5 | pH 6.0 | pH 6.5 | pH 7.0 | pH 8.0 | pH 8.5 | Remarks Megalin measurement (relative value) |
|---|---|---|---|---|---|---|---|
| O.D.(450 nm-630 nm) | | | | | | | |
| 50.00 | 0.991 | 3.7826 | 4.293 | 5.014 | 5.811 | 5.243 | Example |
| 25.00 | 0.479 | 1.0784 | 3.863 | 5.938 | 5.789 | 5.631 | Example |
| 12.50 | 0.257 | 0.359 | 1.610 | 3.492 | 3.466 | 3.527 | Example |
| 6.25 | 0.147 | 0.1568 | 0.569 | 1.530 | 1.516 | 1.438 | Example |
| 3.13 | 0.089 | 0.0823 | 0.199 | 0.528 | 0.501 | 0.546 | Example |
| 1.56 | 0.050 | 0.0486 | 0.083 | 0.184 | 0.196 | 0.185 | Example |
| 0.78 | 0.039 | 0.0373 | 0.049 | 0.083 | 0.089 | 0.087 | Example |
| 0.00 | 0.022 | 0.0168 | 0.019 | 0.023 | 0.022 | 0.020 | Example |

On the other hand, megalin is bonded to various ligands and serves as a scavenger receptor in vivo. The binding between megalin and ligands depends on calcium ions. Upon the addition of a calcium chelating agent and alkalization of the environment, megalin separates from the ligands, whereby the ligand-binding regions, which are characteristic structure of megalin, are exposed on the molecule surface. The pH-dependence of the urinary megalin measurement system is directly influenced by the molecule properties of megalin. The pH-dependent increase in the reactivity of the urinary megalin measurement system is likely due to the exposure of the epitope of the megalin molecular, or the relaxation of steric hindrance between the megalin molecule and anti-megalin antibody. The use of the urinary megalin measuring pretreatment solution utilizing the above-described properties has allowed the immunological detection and quantitation of megalin-specific epitopes, which are normally incognizable, and strongly supports the effects of the urine pretreatment solution composition and the pretreatment method using the same of the present invention.

Example 6

In Example 6, the effect of the addition of the surfactant (Triton X-100) to the urinary megalin measurement system was evaluated. The procedures were the same as in Example 4, except that the loading of the surfactant was changed. The results are shown in Table 6 and FIG. 6.

TABLE 6

| Surfactant proportion (%) | [Megalin] (ng/mL) | | | Remarks Megalin measurement (relative value) |
|---|---|---|---|---|
| | 25.00 | 6.25 | 1.56 | |
| | O.D. (450 nm-630 nm) | | | |
| 0.000 | 0.021 | 0.013 | 0.013 | Comparative example |
| 0.002 | 0.037 | 0.015 | 0.013 | Example |
| 0.010 | 1.246 | 0.337 | 0.013 | Example |
| 0.020 | 3.409 | 0.693 | 0.118 | Example |
| 0.200 | 4.832 | 1.111 | 0.119 | Example |
| 0.500 | 4.683 | 1.116 | 0.125 | Example |
| 1.000 | 4.722 | 1.039 | 0.118 | Example |

Figure 6:
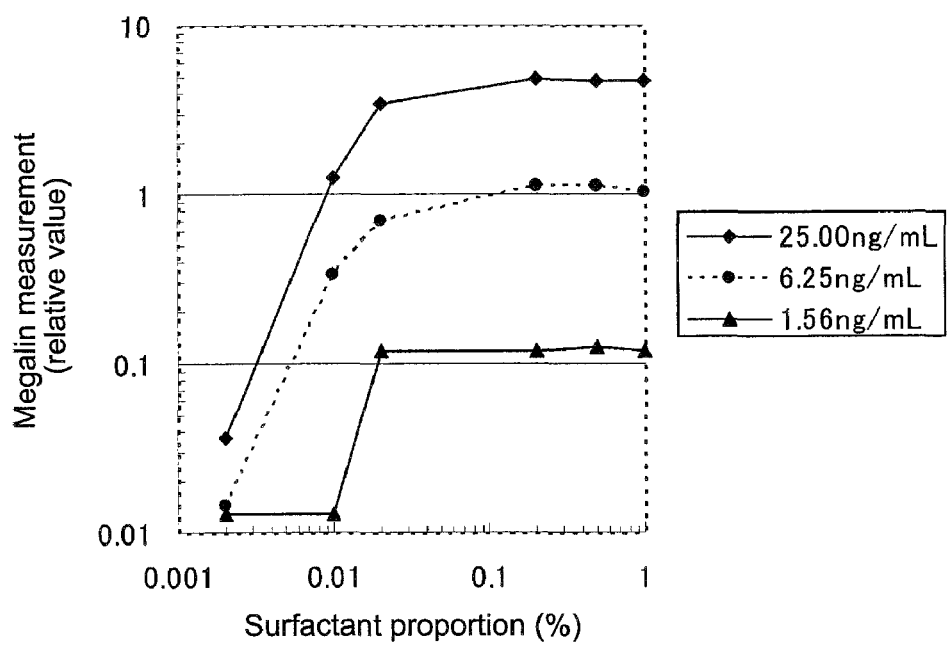
FIG. 6 is a graph showing the blocking effect of the surfactant added to the urine pretreatment agent of the present invention.

As shown in Table 6 and FIG. 6, when Triton X-100 was not added, as the decrease in the megalin antigen concentration, the megalin antigen was lost due to nonspecific adsorption to the test vessel, which resulted in the failure of accurate measurement. On the other hand, when Triton X-100 was added, the blocking effect of Triton X-100 prevented the loss caused by the nonspecific adsorption of the megalin antigen, which allowed the maintenance of accurate measurement. Furthermore, a urine pretreatment solution composition containing a surfactant exhibiting blocking effect and a pretreatment method using the same were able to be provided.

INDUSTRIAL APPLICABILITY

The urine pretreatment agent for urinary protein quantitation, the urine pretreatment method, and the urinary protein quantitation method of the present invention prevent the pH variation between urine samples, dissolve precipitates of urinary inorganic salts, and solubilize membrane proteins. Therefore, they are suitable for the quantitation of urinary podocalyxin and megalin.

The invention claimed is:

1. A urine pretreatment agent for urinary protein quantitation comprising a buffer, a chelating agent, and a surfactant, wherein:
the composition of the urine pretreatment agent is defined by the following formulae (1) to (6):

$$A \geq (20/9) \times X \quad (1)$$

$$B \geq 2000 \times X/9 \times (100-X) \quad (2)$$

$$C \geq (2/9) \times X \quad (3)$$

$$D \geq 200 \times X/9 \times (100-X) \quad (4)$$

$$E \geq 0.2 \quad (5)$$

$$F \geq 20/(100-X) \quad (6)$$

in which:
X (%) represents the proportion of urine in a mixture of urine and the urine pretreatment agent;
A (mM) represents the final concentration of the buffer contained in the mixture of the urine and urine pretreatment agent;
B (mM) represents the concentration of the buffer in a urine pretreatment agent stock solution;
C (mM) represents the final concentration of the chelating agent contained in the mixture of the urine and urine pretreatment agent;
D (mM) represents the concentration of the chelating agent in the urine pretreatment agent stock solution;
E (%) represents the final concentration of the surfactant contained in the mixture of the urine and urine pretreatment agent; and
F (%) represents the concentration of the surfactant in the urine pretreatment agent stock solution.

2. The urine pretreatment agent for urinary protein quantitation according to claim 1, wherein the buffer is a Good's buffer.

3. The urine pretreatment agent for urinary protein quantitation according to claim 1, further comprising at least one acid selected from the group consisting of acetic acid, phosphoric acid, citric acid, boric acid, and tartaric acid.

4. The urine pretreatment agent for urinary protein quantitation according to claim 1, wherein the surfactant is a polyalkylene oxide derivative.

5. The urine pretreatment agent for urinary protein quantitation according to claim 1, wherein the HLB value of the surfactant is from 10 to 18.

6. A urine pretreatment method comprising a step of: mixing 10 to 1000 parts by mass of the urine pretreatment agent according to claim 1 with 100 parts by mass of urine.

7. A urinary protein quantitation method comprising steps of: mixing 10 to 1000 parts by mass of the urine pretreatment agent according to claim 1 with 100 parts by mass of urine; and then measuring the concentration of a protein selected from the group consisting of podocalyxin and megalin.

8. The urinary protein quantitation method according to claim 7, wherein the said protein is podocalyxin.

9. The urinary protein quantitation method according to claim 7, wherein the said protein is megalin.

* * * * *